United States Patent
Tanaka et al.

(10) Patent No.: US 9,408,969 B2
(45) Date of Patent: Aug. 9, 2016

(54) ANESTHETIC SOLUTION-FILLED CARTRIDGE-TYPE ELECTRIC DENTAL SYRINGE

(75) Inventors: Fumio Tanaka, Kawasaki (JP); Mitsuhiro Haraguchi, Shiraoka (JP); Yoshihiko Kawasaki, Tokyo (JP); Mutsumi Shibuya, Yokohama (JP); Renji Hayashi, Matsudo (JP); Yoshinori Kato, Matsudo (JP); Akiko Kawasaki, legal representative, Yokohama-shi (JP)

(73) Assignee: Showa Yakuhin Kako Co., Ltd., Chuo-ku, Tokyo (JP)

( * ) Notice: Subject to any disclaimer, the term of this patent is extended or adjusted under 35 U.S.C. 154(b) by 603 days.

(21) Appl. No.: 13/997,864

(22) PCT Filed: Dec. 27, 2010

(86) PCT No.: PCT/JP2010/073575
§ 371 (c)(1),
(2), (4) Date: Jul. 17, 2013

(87) PCT Pub. No.: WO2012/090273
PCT Pub. Date: Jul. 5, 2012

(65) Prior Publication Data
US 2014/0011158 A1    Jan. 9, 2014

(51) Int. Cl.
*A61M 5/20*    (2006.01)
*A61M 5/24*    (2006.01)
(Continued)

(52) U.S. Cl.
CPC ............... *A61M 5/20* (2013.01); *A61C 19/08* (2013.01); *A61M 5/24* (2013.01); *A61M 5/31511* (2013.01); *A61C 5/062* (2013.01); *A61M 2005/31518* (2013.01)

(58) Field of Classification Search
CPC ...... A61M 5/20; A61M 5/31511; A61M 5/24; A61M 2005/31518; A61C 19/08; A61C 5/062
See application file for complete search history.

(56) References Cited

U.S. PATENT DOCUMENTS 7,291,132 B2    11/2007    DeRuntz et al.
7,427,275 B2    9/2008    DeRuntz et al.
(Continued)

FOREIGN PATENT DOCUMENTS

EP    2 238 999 A1    10/2010
JP    2005-245852 A    9/2005
(Continued)

OTHER PUBLICATIONS

European Patent Office, Extended Search Report for European Patent Application No. 10 861 302.7, May 2, 2014, Munich, Germany.

*Primary Examiner* — Kevin C Sirmons
*Assistant Examiner* — Amber Stiles
(74) *Attorney, Agent, or Firm* — Taft Stettinius & Hollister LLP (57) ABSTRACT

Provided is an anesthetic solution-filled cartridge-type electric dental syringe, wherein the plunger has been shortened but the plunger can nevertheless be extended to the distance necessary to evacuate the anesthetic solution from the cartridge. The syringe comprises: an extension tube into which a plunger is movably inserted, the extension tube being movably disposed in the through hole of a support block and having racks formed in the side surface thereof that are coordinated with the racks of the plunger; and a means for the plunger to draw the extension tube to engage the racks of the extension tube with a pinion when the plunger reaches the middle of the distance corresponding to the anesthetic solution accommodation length of the cartridge. By the engagement of the racks of the extension tube with the pinion, the plunger moves together with the extension tube for the remainder of the distance corresponding to the anesthetic solution accommodation length of the cartridge.

3 Claims, 7 Drawing Sheets

(51) Int. Cl.
*A61M 5/315* (2006.01)
*A61C 19/08* (2006.01)
*A61C 5/06* (2006.01)

(56) References Cited

U.S. PATENT DOCUMENTS

| 2005/0197650 | A1 | 9/2005 | Sugimoto et al. |
| 2006/0206057 | A1 | 9/2006 | DeRuntz et al. |
| 2008/0097325 | A1 | 4/2008 | Tanaka et al. |
| 2009/0054832 | A1 | 2/2009 | Sugimoto et al. |
| 2009/0062777 | A1 | 3/2009 | Sugimoto et al. |
| 2012/0035542 | A1 | 2/2012 | Pongprairochana |

FOREIGN PATENT DOCUMENTS

| WO | 96/26754 A2 | 9/1996 | |
| WO | 2005/018721 A1 | 3/2005 | |
| WO | 2006/090509 A1 | 8/2006 | |
| WO | WO 2010089313 A1 * | 8/2010 | ........ A61M 5/14566 |

* cited by examiner

ANESTHETIC SOLUTION-FILLED CARTRIDGE-TYPE ELECTRIC DENTAL SYRINGE

TECHNICAL FIELD

This invention relates to anesthetic solution-filled cartridge-type motorized syringes, and particularly, to such a motorized syringe in which an improved pusher rod is incorporated to push a plunger rubber plug in the cartridge for delivery of the anesthetic solution filled in the cartridge.

BACKGROUND OF THE INVENTION

The cartridge is made of glass and has a dental anesthetic solution filled therein for local anesthesia. There are cartridges of 1.8 ml and 1.0 ml of anesthetic in volume and they are different in length due to the different volumes of anesthetic and due to the fact that the cartridges have identical inner and outer diameters.

In either case, a motorized syringe may used for administration of anesthesia by loading a cartridge into a cartridge holder, detachably connecting the cartridge holder to a coupling of the motorized syringe, and affixing a double pointed needle to the tip of the cartridge. The motorized syringe comprises a pusher rod for pushing a plunger rubber plug in the cartridge to deliver anesthetic solution from the cartridge through the needle, and an operating mechanism for advancing the plunger rod. The operating mechanism generally, includes a pinion rotated through a power transmission from a drive unit which includes a drive motor and a reduction gear, and a rack formed on the pusher rod and in engagement with the pinion. In order to deliver the entire anesthetic solution from the cartridge loaded in the cartridge holder, the pusher rod must be moved a distance equal to the length of accommodation of anesthetic solution in the cartridge while pushing the plunger rubber plug in the cartridge by advancement of the pusher rod with its rack engaging the rotating pinion. The distance of movement of the pusher rod is defined by bringing a limit switch into an off-state by the rear end of the pusher rod to stop the rotation of the motor. After delivery of anesthetic solution, the cartridge holder is detached from the coupling and the power transmission from the drive unit is interrupted to bring the pinion into an idle state. The pusher rod can thus pushed into the syringe body the identical distances by hand. In this process, the limit switch is brought into an on-state by the outer surface of the pusher rod. The pusher rod must be configured to extend rearwardly from the pinion by a length that is equal to the length of accommodation of anesthetic solution in the cartridge plus a length equal to a distance between the pinion and the limit switch is. To this end, the pusher rod for the motorized syringe must be long in size, and consequently, the motorized syringe must be designed in a long and bulky configuration. From the foregoing, an appearance of a relatively compact cartridge-type motorized syringe has been strongly desired from dental practitioners.

DISCLOSURE OF THE INVENTION

An object of the present invention is to provide a dental anesthetic solution-filled cartridge-type motorized syringe which has a shorter pusher rod in order to comply with such wishes, and nonetheless makes it possible to move the pusher rod the necessary distance to deliver anesthetic solution from the cartridge.

The object of the invention can be achieved by providing a dental anesthetic solution-filled cartridge-type motorized syringe wherein engagement of a pinion rotated by a drive unit with a rack on a pusher rod, causes it to slowly move, thereby moving a plunger rubber plug in the cartridge for delivery of anesthetic solution from the cartridge through a needle, characterized by comprising an extension tube movably located in a through-hole in a support block into which the pusher rod is movably inserted, and having racks formed on sides of the extension tube in alignment with the rack on the pusher rod, means for the pusher rod to pull the extension tube to engage the racks on the extension tube with the rotating pinion when the pusher rod reaches the middle of a distance equal to a length of accommodation of anesthetic solution in the cartridge, the engagement of the racks on the extension tube with the pinion causing the pusher rod to move a remainder of the distance equal to length of accommodation of anesthetic solution in the cartridge, together with extension tube.

In a preferred embodiment of the invention, the motorized syringe comprises means for releasably coupling the pusher rod to the support block to prevent the extension tube from moving relative to the support block during movement of the pusher rod, the coupling means including a locking ball received in a hole formed in a portion of the extension tube adjacent to its forward end, and a recess formed in the through-hole in the support block, with a portion of the locking ball in the hole, which is pushed out of the outer surface of extension tube by the circular outer surface of the pusher rod, engaging the recess for connection of the extension tube to the support block. There is further provided a recess facing the locking ball and formed on the outer surface of the pusher rod for release of the coupling of the extension tube to the support block, when the pusher rod reaches the middle of the distance equal to the length of accommodation of anesthetic solution in the cartridge.

The extension tube may preferably include a forward portion having an inner diameter equal to the outer diameter of the pusher rod and a rearward portion having an inner diameter larger than the inner diameter of the forward portion. A shoulder is defined between the forward portion and the rearward portion, and means for pulling the extension tube may comprise protrusions provided on the pusher rod adjacent to its rear end and adapted to abut the shoulder by moving in the rearward portion of the extension tube.

BEST MODE FOR CARRYING OUT THE INVENTION

Figure 1:
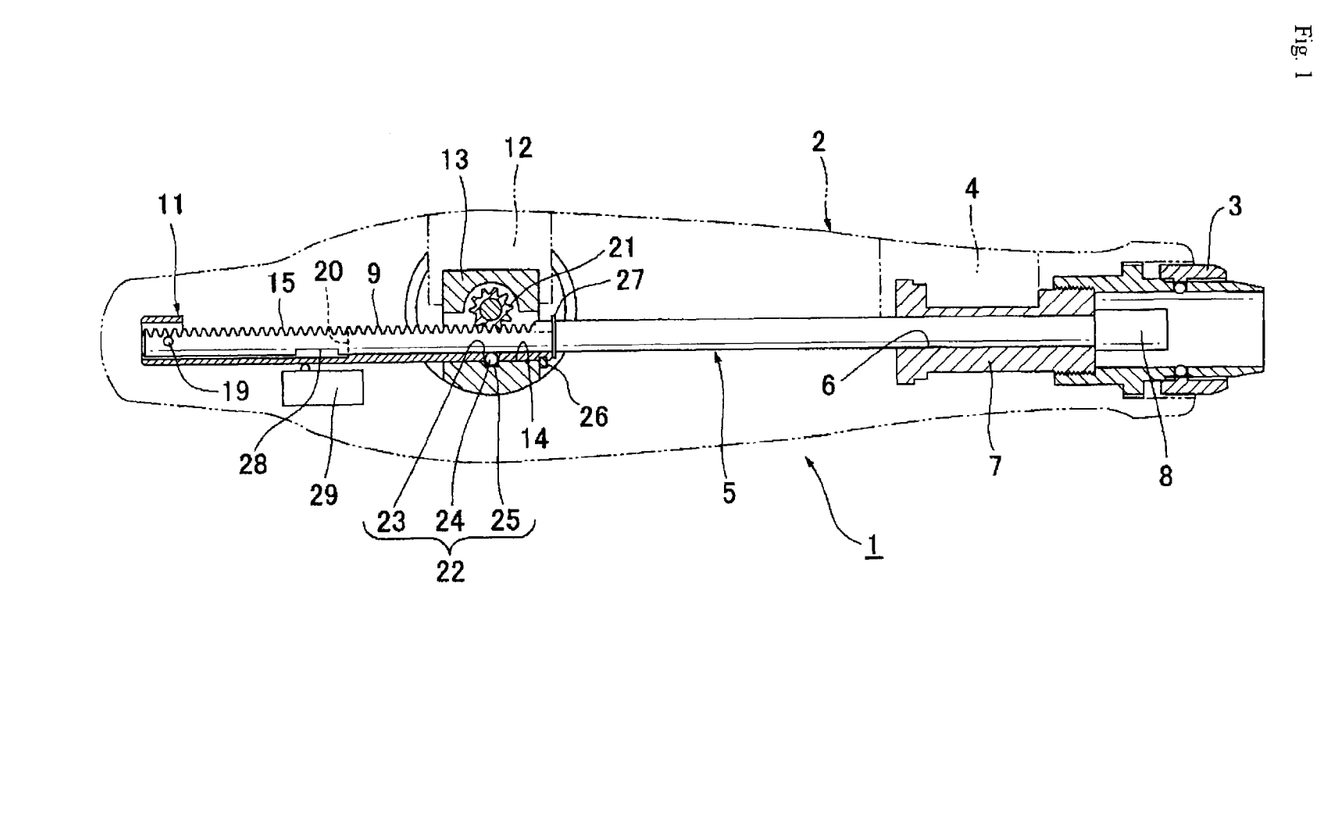
FIG. 1 is a top plan view of a dental anesthetic solution-filled cartridge-type motorized syringe with a pusher rod according to the invention provided therein.
Figure 2:
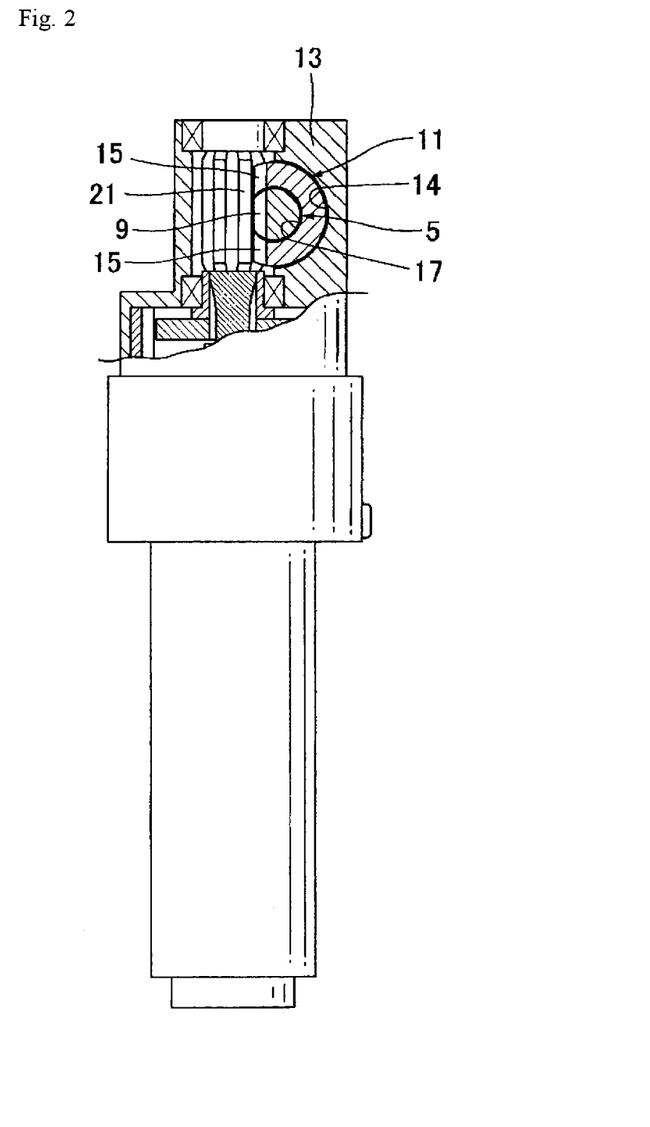
FIG. 2 is an elevation view of the dental anesthetic solution-filled cartridge-type motorized syringe with its portion cut away to show a pinion and rack.
Figure 3:
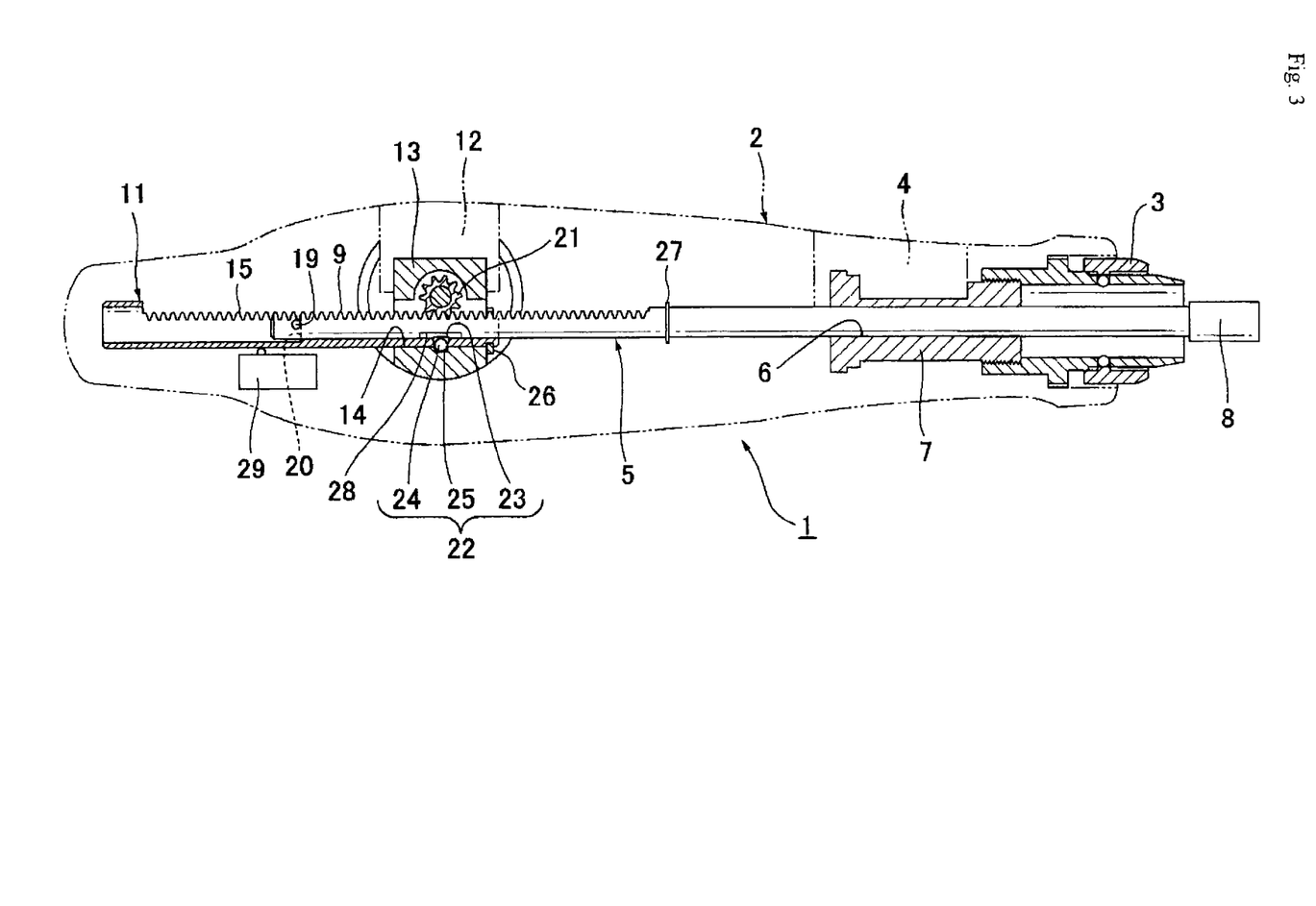
FIG. 3 is a view substantially similar to FIG. 1 with the pusher rod moved up to the middle of the distance equal to the length of accommodation of anesthetic solution in the cartridge.
Figure 4:
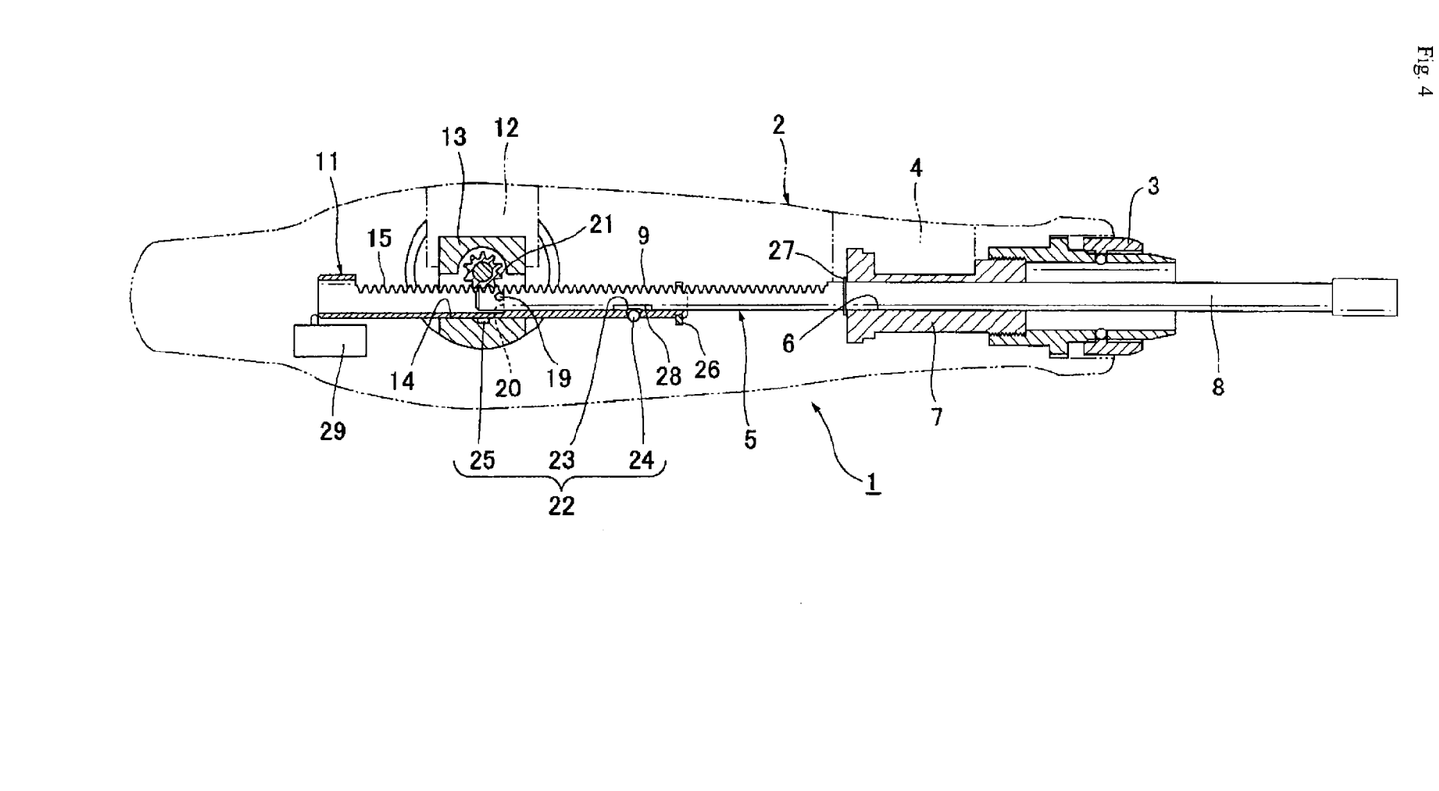
FIG. 4 is a view substantially similar to FIG. 1 with the pusher rod moved, together with an extension tube, a remainder of the distance equal to the length of accommodation of anesthetic solution in the cartridge.
Figure 5:
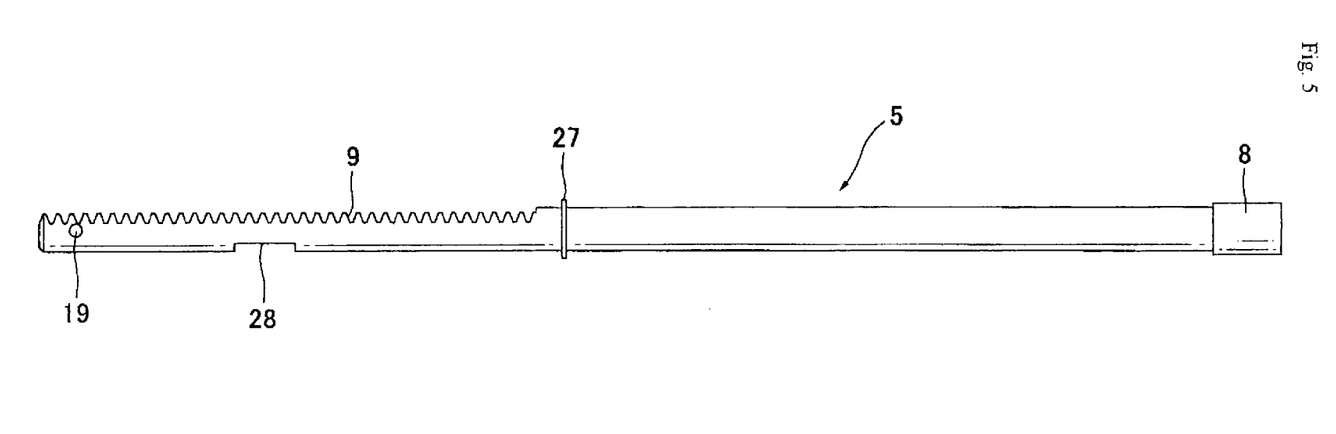
FIG. 5 is a top plan view of the pusher rod.
Figure 6:
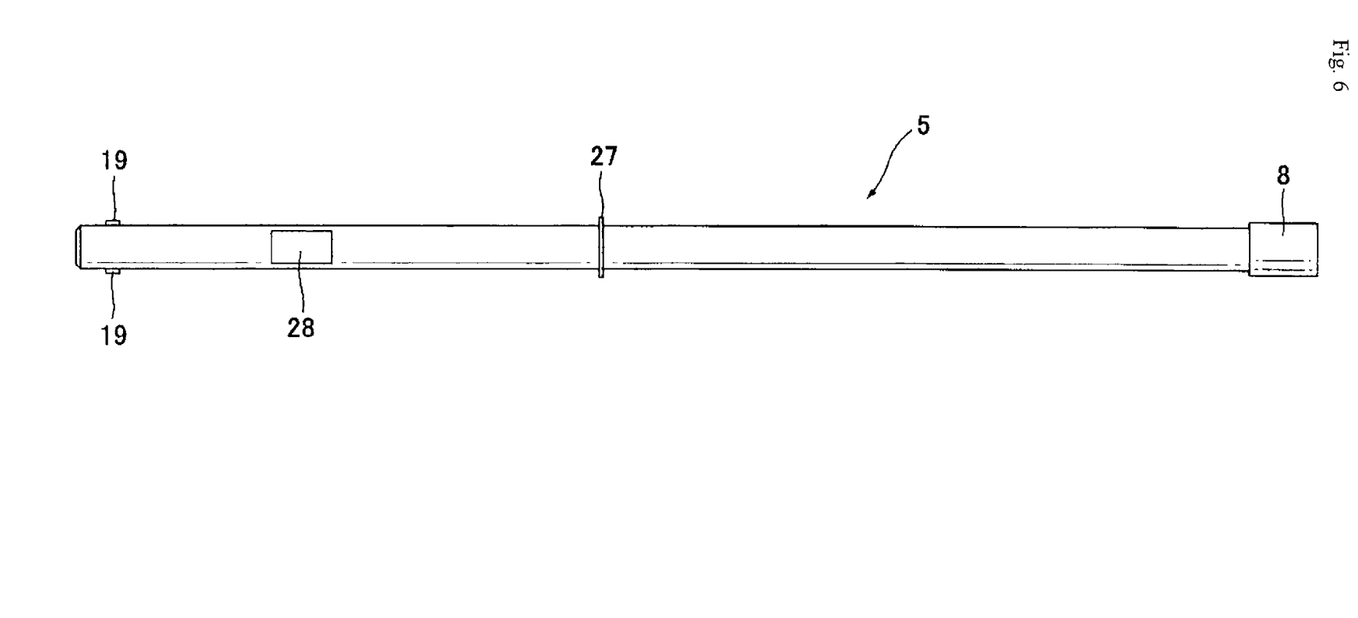
FIG. 6 is a side elevation view of the pusher rod.

Referring to FIG. 1 of the drawings, a motorized syringe 1 embodied in accordance with the invention includes a syringe body 2 as generally indicated in a dotted line and a coupling 3 for detachably connecting a cartridge holder (not shown) to the forward end of the syringe body, the cartridge holder having an anesthetic solution-filled cartridge (not shown) loaded thereinto. The coupling 3 is threadedly affixed to a support member 7 secured to a mounting block 4 and having a through-hole 6 through which a metallic round pusher rod 5 is passed.

Figure 7:
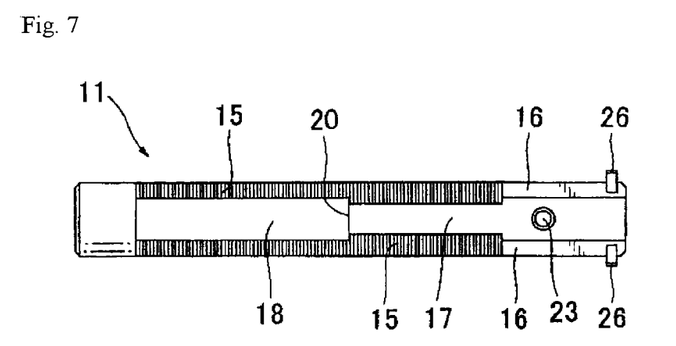
FIG. 7 is a side elevation view of the extension tube.
Figure 8:
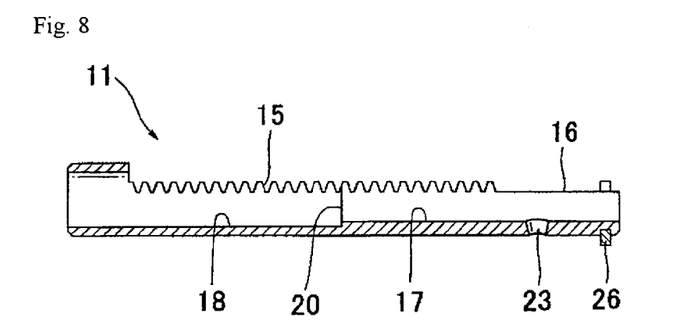
FIG. 8 is a top plan view in section of extension tube.

As shown in FIG. 1 and FIGS. 3-6, pusher rod 5 is provided with an enlarged head 8 adapted to abut a plunger rubber plug (not shown) in the cartridge, from behind, and is formed on its rearward portion with a flat rack 9 on one side of pusher rod 5. As can be seen in FIGS. 1-4, a metallic extension tube 11 is movably inserted in a through hole 14 in a support block 12 affixed to a mounting block of syringe body 2, such that pusher rod 5 is received in the interior of the extension tube 11. As can be seen in FIGS. 7 and 8, extension tube 11 is formed with racks 15, 15 on a portion horizontally removed up to a point adjacent the rear end thereof in a plan common to and on both sides of the rack 9 on pusher rod 5. Extension tube 11 has flat surfaces 16, 16 on a forward portion thereof for reasons described below. Extension tube 11 includes a hollow forward portion 17 having an interior diameter equal to an exterior diameter of the pusher rod 5, up to a point adjacent to half of the longitudinal length of racks 15, 15 and a hollow rearward portion 18 having an interior diameter larger than the interior diameter of the hollow forward portion 17, such that protrusions 19, 19 extending radially outwardly from the pusher rod 5 adjacent its rear end can move in the interior of hollow rearward portion 18. Thus, the rear end face of the inner surface of the hollow forward portion 17 defines a shoulder 20 which protrusions 19, 19 abut when the pusher rod 5 moves forwardly relative to the extension tube 11.

Motorized syringe 1 includes a drive unit including a motor and reduction gear, having a pinion 21 fixedly connected to a drive shaft thereof, and journaled in support block 13, the pinion 21 being adapted to engage racks 9 on pusher rod 5 and subsequently rack 9 and racks 15, 15 on the extension tube 11. In order to define a retracted position of the extension tube 11, there is provided means 22 for coupling the extension tube 11 to support block 13 to prevent extension tube 11 from being moved relative to support block 13. The coupling means comprises a locking ball 24 received in hole 23 formed in the forward portion of extension tube 11, and a recess 25 formed in the inner surface of through-hole 14 to receive a portion of locking ball 24 when it is pushed out of the outer surface of extension tube 11 by the outer surface of pusher rod 5. When extension tube 11 is coupled to support block 13, pinion 21 is always in engagement with rack 9 on pusher rod 5, but is adapted not to engage racks 15, 15 on the extension tube due to the fact that the pinion 21 faces the non-rack tooth flat surface of the extension tube.

Assuming that a distance of movement of pusher rod 5 which corresponds to a length of accommodation of the anesthetic solution in a cartridge is 50 mm, protrusions 19, 19 are positioned to engage shoulder 20 when pusher rod 5 moves forward its half distance, that is, 25 mm.

A stop ring 26 is fitted at the forward end of extension tube 11 to abut the front surface of support block 13, thereby restricting a retracted position of the extension tube. In order to push extension tube 11 back to its retracted position in response to the retraction of pusher rod 5 and to restrict a retracted position of pusher rod 5, a stop ring 27 is located on pusher rod 5 at a position adjacent to the rack 9 to abut the front end face of extension tube 11.

It is assumed that an anesthetic solution-filled cartridge (not shown) is loaded into a cartridge holder (not shown) which is then connected to syringe 1 by means of coupling 3, and pusher rod 5 and extension tube 11 are brought to their retracted positions (see FIG. 1). Since as described above, extension tube 11 is coupled to the support block 13 by engagement of locking ball 24 with recess 25, the extension tube remains in the retracted position. Pinion 21 is rotated through the power transmission of the drive unit and engagement of rotating pinion with rack 9 causes pusher rod 5 to move forward, pushing a plunger rubber plug (not shown) in the cartridge. The anesthetic solution is thus delivered from the cartridge through the needle. At the time when protrusions 19, 19 on pusher rod 5 engage shoulder 20, recess 28 which is formed in the circular outer surface of pusher rod 5 faces locking ball 24 in hole 23 to escape locking ball 24 from recess 25 into recess 28, thereby releasing the coupling of the extension tube to support block 13 (see FIG. 3). Forward continuous movement of pusher rod 5 permits extension tube 11 to be pulled, due to engagement of protrusions 19, 19 with shoulder 20, to the position where racks 15, 15 can engage rotating pinion 21. The engagement of rotating pinion 21 with both rack 9 on pusher rod 5 and racks 15, 15 on extension tube 11, causes pusher rod 5 and extension tube 11 to move forward together, a distance equal to the length of accommodation of the anesthetic solution in the cartridge. At this point, limit switch 29 is brought into an off-position to de-energize the motor in the drive unit.

After delivery of the injection solution, the cartridge holder is detached from the coupling and simultaneously, the power transmission of the drive unit to the pinion is interrupted to bring it into an idle state where the pusher rod can be pushed back into the syringe body by hand. Since pinion 21 is in engagement with rack 9 on pusher rod 5 and racks 15, 15 on extension tube 11, the extension tube are pushed back together with the pusher rod without any relative movement between them. The movement of extension tube 11 is stopped by abutment of stop ring 26 against support block 13. At substantially the same time, the non-tooth flat surface 16, 16 of extension tube 11 facing the pinion and locking ball 24 also faces recess 25 so that by partially forcing locking ball out of recess 23 with the circular outer surface of pusher rod 5, a portion of locking ball 24 will be engaged in recess 25 to couple extension tube 11 to support block 13. Only pusher rod 5 continues to be pushed back but the movement of the pusher rod is stopped by abutment of stop ring 27 against the front end face of extension tube 11 (see FIG. 1).

According to the invention, the pusher rod can be shortened by a length equal to a distance between the limit switch and the pinion to provide a relatively compact cartridge-type motorized dental syringe, since in the middle of forward movement of the pusher rod a distance equal to the length of accommodation of anesthetic solution in the cartridge, the extension tube is moved forward, together with the pusher rod, by means of the rack and pinion.

What is claimed is:

1. A dental anesthetic solution-filled cartridge-type motorized syringe, comprising a pinion rotated by a drive unit with a rack on a pusher rod,
   wherein engagement of the pinion rotated by the drive unit with the rack on the pusher rod causes the pusher rod to move, thereby moving a plunger rubber plug in a cartridge for delivery of anesthetic solution from the cartridge through a needle, characterized by comprising
   an extension tube movably located in a through-hole in a support block into which the pusher rod is movably inserted, and having racks formed on sides of the extension tube in alignment with the rack on the pusher rod, the extension tube comprising
a forward portion having an inner diameter equal to an outer diameter of the pusher rod,
a rearward portion having an inner diameter larger than the inner diameter of the forward portion,
a shoulder defined between the forward portion and the rearward portion, and
protrusions provided on the pusher rod adjacent the rear end of the pusher rod and adapted to abut the shoulder by moving in the rearward portion of the extension tube, thereby pulling the extension tube to engage the racks on the extension tube with the rotating pinion when the pusher rod reaches a middle of a distance equal to a length of accommodation of anesthetic solution in the cartridge, wherein the engagement of the racks on the extension tube with the pinion causes the pusher rod to move a remainder of the distance equal to the length of accommodation of anesthetic solution in the cartridge, together with the extension tube.

2. A dental anesthetic solution-filled cartridge-type motorized syringe according to claim 1, further comprising wherein in order to prevent the extension tube from moving relative to the support block during movement of the pusher rod, there is further provided a coupling including a locking ball received in a hole formed in a portion of the extension tube adjacent to a forward end of the extension tube, and a recess formed in the through-hole in the support block, with a portion of the locking ball in the hole, which is pushed out of an outer surface of the extension tube by a circular outer surface of the pusher rod, engaging the recess for connection of the extension tube to the support block.

3. A dental anesthetic solution-filled cartridge-type motorized syringe according to claim 2, further comprising a recess facing the locking ball and formed on the outer surface of the pusher rod for release of the coupling of the extension tube to the support block, when the pusher rod reaches the middle of the distance identical to the length of accommodation of anesthetic solution in the cartridge.

* * * * *